(12) United States Patent
Perkins et al.

(10) Patent No.: US 6,398,775 B1
(45) Date of Patent: Jun. 4, 2002

(54) APPARATUS AND METHOD FOR ISOLATED LUNG ACCESS

(75) Inventors: Rodney A. Perkins, Woodside; Peter P. Soltesz, San Jose; Robert Kotmel, Burlingame, all of CA (US)

(73) Assignee: Pulmonx, Palo Alto, CA (US)

( * ) Notice: Subject to any disclaimer, the term of this patent is extended or adjusted under 35 U.S.C. 154(b) by 0 days.

(21) Appl. No.: 09/425,272

(22) Filed: Oct. 21, 1999

(51) Int. Cl.$^7$ ............................................. A61M 31/00
(52) U.S. Cl. .................... 604/514; 604/35; 604/107.03; 604/164.03; 604/164.13
(58) Field of Search ................................ 604/96.01, 28, 604/35, 43, 500, 514, 101.04, 101.02, 102.03, 164.01, 164.03, 164.13, 171, 523, 912, 915

(56) References Cited

U.S. PATENT DOCUMENTS

| | | |
|---|---|---|
| 4,453,545 A | 6/1984 | Inoue |
| 4,714,460 A | * 12/1987 | Calderon |
| 4,716,896 A | 1/1988 | Ackerman ............. 128/200.26 |
| 5,207,220 A | 5/1993 | Long |
| 5,285,778 A | 2/1994 | Mackin ................. 128/207.15 |
| 5,309,903 A | 5/1994 | Long |
| 5,653,231 A | 8/1997 | Bell |
| 5,660,175 A | 8/1997 | Dayal |

FOREIGN PATENT DOCUMENTS

WO WO 92/10971 7/1992

* cited by examiner

Primary Examiner—Brian L. Casler
Assistant Examiner—Jeremy Thissell
(74) Attorney, Agent, or Firm—Townsend and Townsend and Crew LLP

(57) ABSTRACT

Apparatus, systems, methods, and kits are provided for isolating a target lung segment and treating that segment, usually by drug delivery or lavage. The systems include at least a lobar or sub-lobar isolation catheter which is introduced beyond a second lung bifurcation (i.e., beyond the first bifurcation in a lobe of the lung) and which can occlude a bronchial passage at that point. An inner catheter is usually introduced through the isolation catheter and used in cooperation with the isolation catheter for delivering and/or removing drugs or washing liquids from the isolated lung region. Optionally, the inner catheter will also have an occluding member near its distal end for further isolation of a target region within the lung.

34 Claims, 15 Drawing Sheets

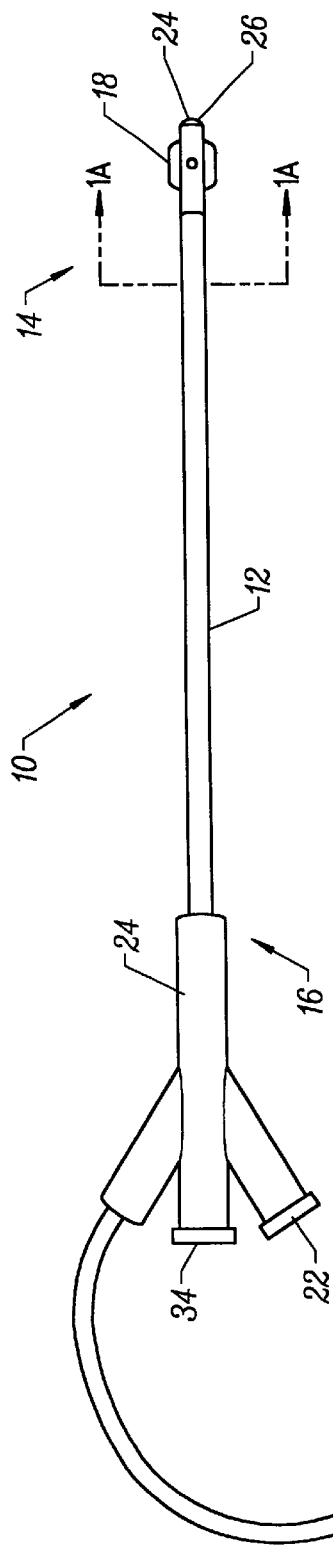
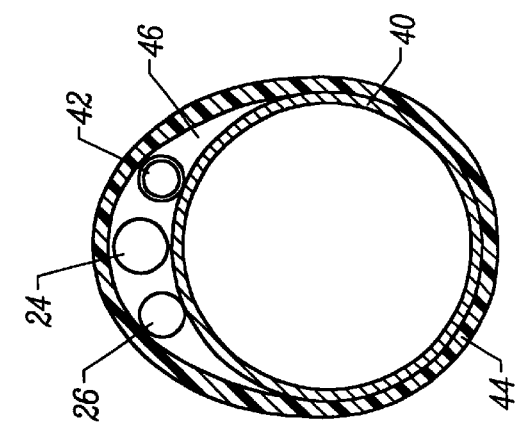
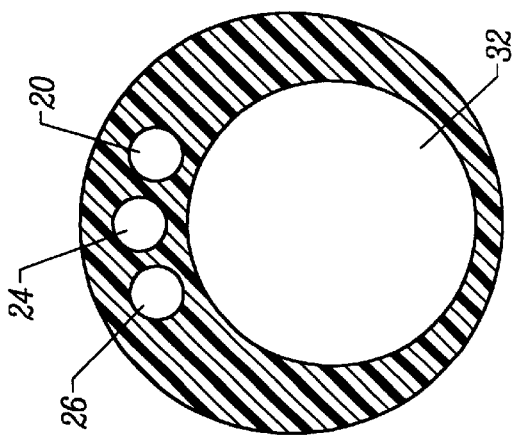
FIG. 1
FIG. 1B
FIG. 1A

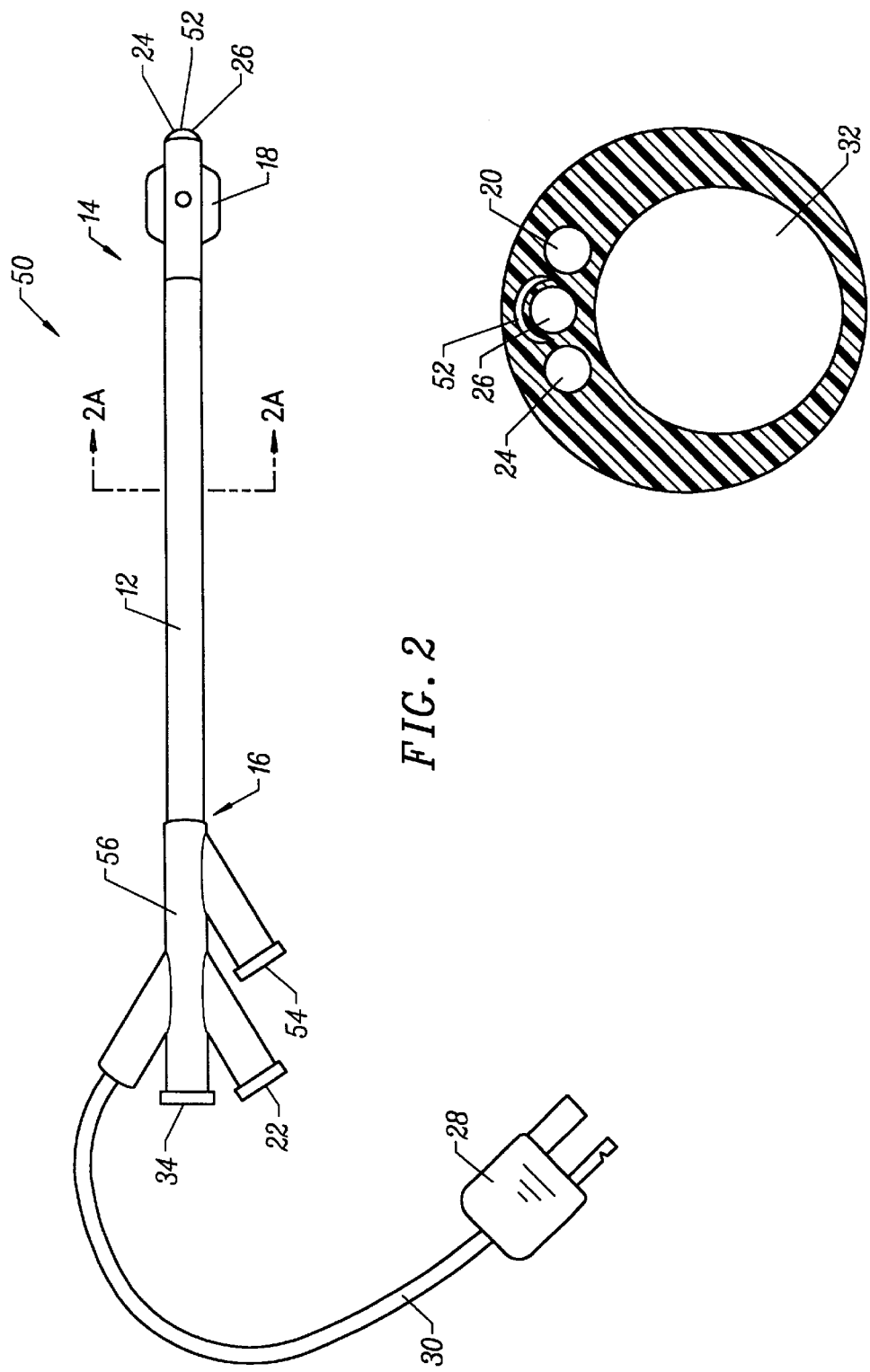

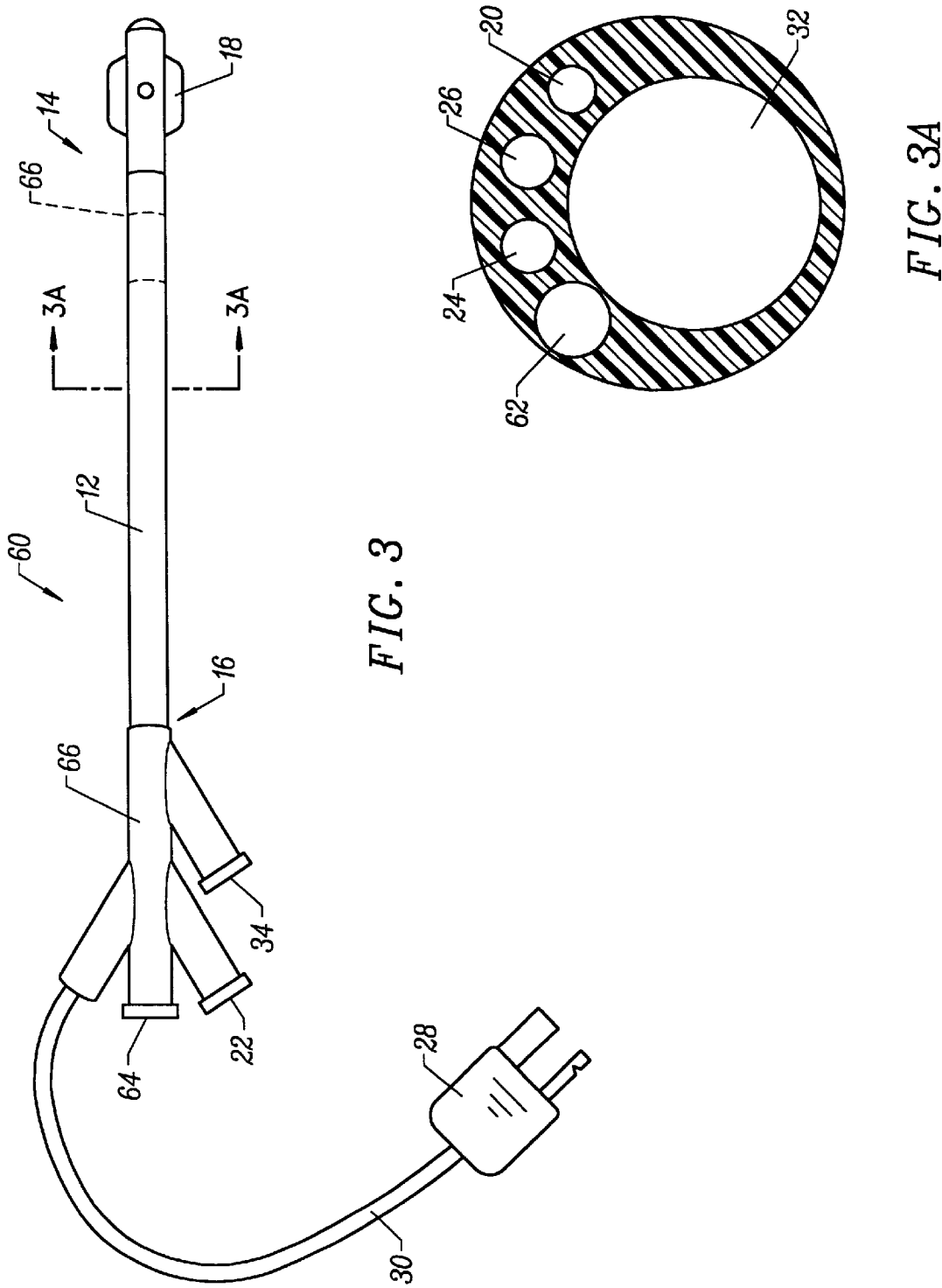

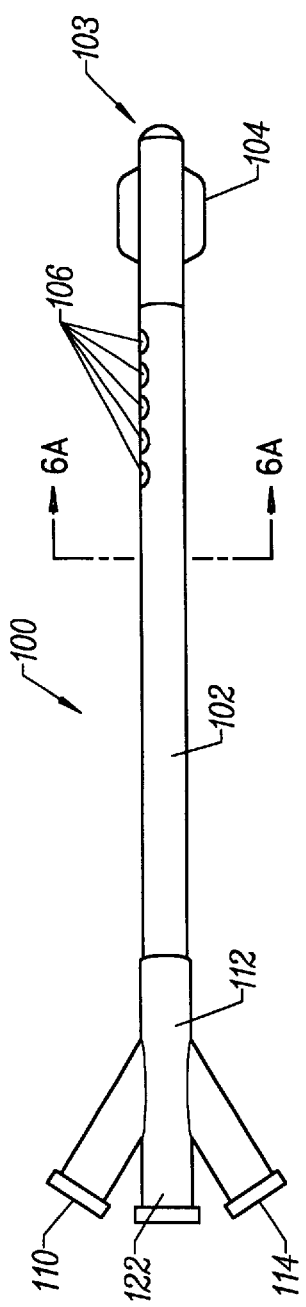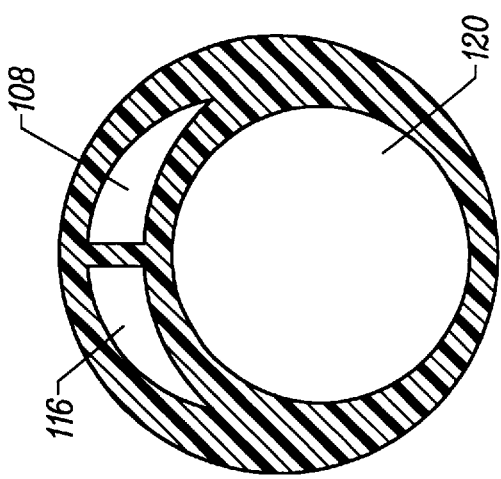
FIG. 6
FIG. 6A

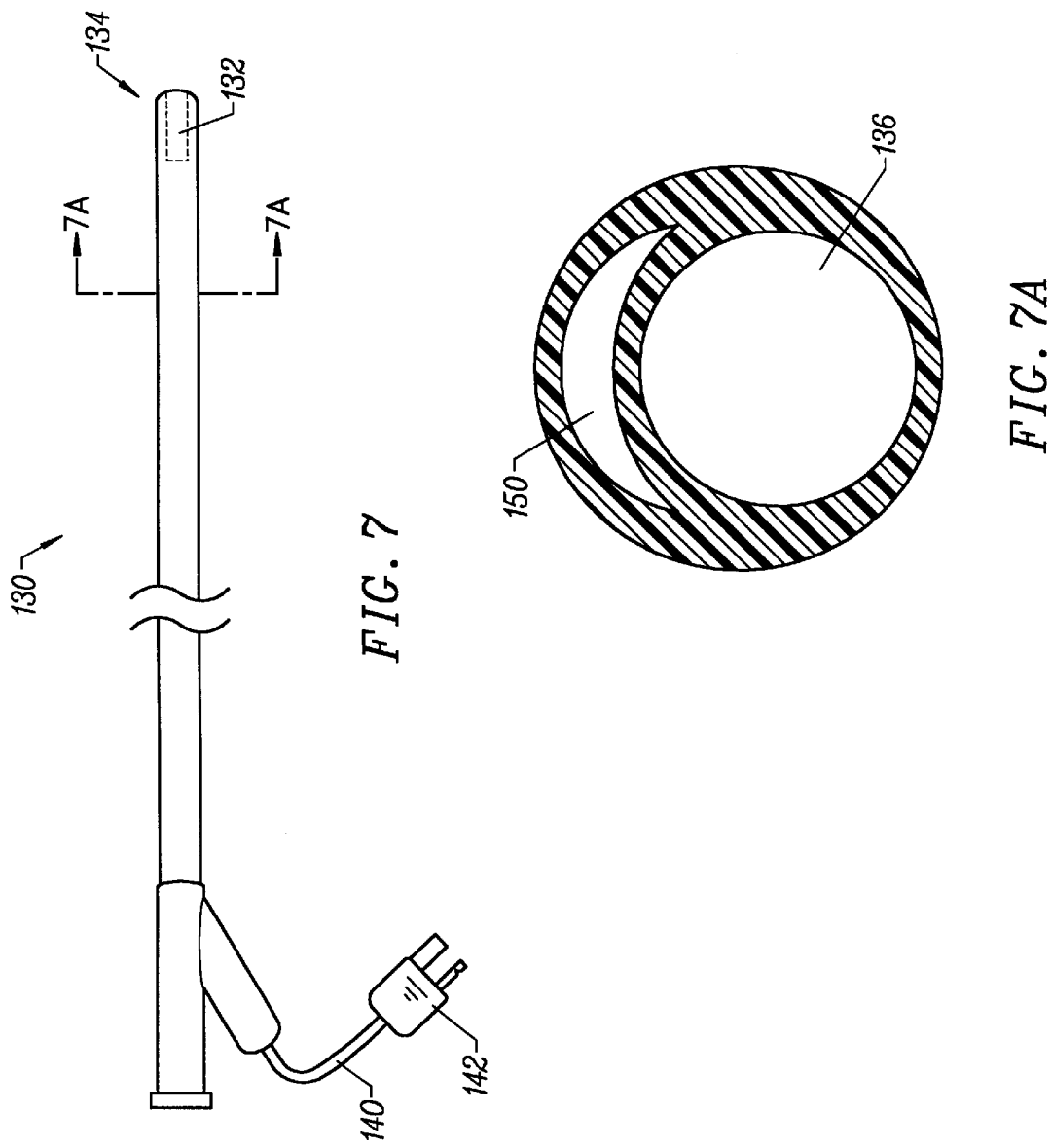

APPARATUS AND METHOD FOR ISOLATED LUNG ACCESS

BACKGROUND OF THE INVENTION

1. Field of the Invention

The present invention relates generally to medical apparatus, systems, methods, and kits. More particularly, the present invention relates to methods and apparatus for isolating sub-bronchial regions of the lung and delivering or retrieving substances from such isolated regions.

Lung access and isolation is of interest in numerous therapeutic and diagnostic medical procedures. In particular, access to the lungs is useful for both local and systemic drug delivery, lung lavage, visual assessment and diagnosis of lung function, and the like.

For drug delivery, access is most simply achieved by introducing an aerosol to the lungs through the mouth or nose, and a variety of inhalers, nebulizers, metered dose inhalers (MDIs), nasal sprayers, and the like, have been developed over the years. While very effective for many drugs, delivery through the mouth or nose can be very inefficient, often with less than 20% of the drug reaching circulation or a targeted local treatment region. Moreover, inhalation through the mouth or nose is not able to target drug delivery to a particular region of the lungs. While this may not be a problem for systemic delivery, it can be a significant drawback in the treatment of localized disease where a highly controlled delivery profile would be preferred.

In an effort to overcome at least some of these shortcomings, a variety of endotracheal drug delivery and lung lavage systems have been developed. Most simply, an endotracheal or tracheostomy tube having an inflatable cuff at its distal end may be placed in a patient's trachea and used to deliver a drug aerosol to the whole of the lungs. While this can improve the efficiency of drug delivery (reducing the amount of drug deposited in the nasal passages or throat), it helps little in targeting treatment within any particular region of the lungs. Thus, it has been further proposed to use a secondary catheter placed through an endotracheal or tracheostomy tube for selectively isolating the left or right bronchus. For example, the secondary catheter can have an inflatable cuff which is positioned immediately beyond the main branching between the left and right bronchi. One of the bronchi can then be accessed through the secondary catheter while the other is accessed through the tracheal tube. Such systems are described, for example, in U.S. Pat. Nos. 5,285,778 and 5,660,175. While such systems offer significant benefits over the use of an endotracheal tube by itself, they still do not permit isolation of sub-bronchial regions of the lung for drug delivery, lavage, or any other purpose.

A system for bronchoalveolar lavage which can isolate a sub-bronchial region of the lung is described in published Application No. WO 92/10971. A co-axial catheter system is placed through an endotracheal tube, with the inner most catheter having an isolation wedge or balloon which can be positioned in a remote bronchiole to effect isolation of a distal region of the lung. The outer catheter has no capability for isolating the lung and is used, for example, for ventilating the lung proximal to the isolation cuff. While potentially an improvement over prior systems, the apparatus of WO 92/10971 will be very difficult to position, making targeting of particular sub-bronchial regions very difficult. Moreover, the inability to isolate a bronchus upstream from the distal isolation cuff limits the ability to selectively treat different regions of the bronchus in different ways. That is, while the particular sub-bronchial region which is isolated by the distal isolation cuff may be treated in one way, the remainder of that bronchus as well as the entire other lung must be ventilated and treated in a common manner through either the endotracheal tube or the outer catheter of the co-axial catheter pair.

For these reasons, it would be desirable to provide improved apparatus, systems, methods, and kits for the treatment and diagnosis of selected regions of a patient's lungs, particularly a lobar or targeted sub-lobar regions of the patient's lungs. The present invention should provide for the efficient delivery of pharmaceutical and other substances to the targeted sub-lobar regions of the lung. Moreover, in some embodiments, the present invention should be able to provide at least a second level of isolation within a particular bronchus and/or the ability to instill the pharmaceuticals or other substances at a point significantly distal to a point of isolation within the bronchus. The systems and apparatus of the present invention should be capable of being positioned precisely to a targeted bronchi within the bronchus, preferably providing on-board visualization while components of the system are positioned over a guidewire. Additionally, the apparatus, systems, methods, and kits of the present invention should be suitable for a wide variety of purposes, including pharmaceutical drug delivery, lung lavage (optionally in combination with drug delivery), diagnosis (optionally in combination with lung lavage), and the like. In particular, the present invention should be useful for localized drug delivery where a particular drug or other therapeutic agent can be delivered to a well-defined, isolated sub-bronchial region of the lung (as defined hereinafter) with little or no delivery to other regions of the lung. At least some of these objectives will be met by the inventions described hereinafter.

2. Description of the Background Art

WO 92/10971 describes a bronchoalveolar lavage catheter system having an outer catheter and an inner catheter with an enlarged (optionally inflatable) tip which is advanced until the tip wedges in a bronchiole of the patient. A region of the lungs distal to the enlarged tip may then be lavaged to retrieve sample. U.S. Pat. Nos. 5,660,175; 5,653,231; 4,716,896; and 4,453,545, describe single and co-axial catheter systems for accessing a patient's lungs. U.S. Pat. No. 5,285,778, describes a co-axial endoscopic lung access system. U.S. Pat. Nos. 5,309,903 and 5,207,220 describe systems for administering liquid pharmaceutical formulations to an isolated lung.

SUMMARY OF THE INVENTION

The present invention provides improved apparatus, systems, methods, and kits for isolating lobar and sub-lobar regions of a patient's lungs. The isolated region will be a portion (not the whole) of the right or left lung, and isolation will be accomplished by occluding a bronchial passage at at least one location in the lobar, segmental, and subsegmental bronchus. Thus, a primary occlusion will be formed after both the main bifurcation of the trachea and a further bifurcation into the lobar bronchus. Optionally, the lobar and/or sub-lobar region can be further isolated at at least one secondary location distal to the primary point of isolation and usually after further branching of the bronchial passages. Isolation at the primary location and optional additional locations within the bronchial passages will usually be effected by expansion of an occlusion member, such as an inflatable cuff, inflatable balloon, or the like.

Once the lobar or sub-lobar region has been isolated, a variety of therapeutic and diagnostic procedures can be performed within the isolated region. For example, pharmaceutical formulations including small molecule drugs, biological macromolecular drugs, and the like, can be specifically delivered to the isolated region with minimal or no cross-delivery to other regions of the lungs. Similarly, lavage may be performed within the isolated region with minimal impact on adjacent regions of the lungs. Isolation of the lobar or sub-lobar region permits such drug delivery and lavage procedures to be further controlled by control of the volumes, rates, pressures, temperatures, repetitions, retention times, and other method and system parameters. For example, the pressure within the isolated region can be controlled separately from the pressure or pressures maintained outside of the isolated region. In this way, a variety of delivery parameters can be controlled. By elevating pressure within the isolated region above that in the surrounding regions of the lung, the isolated lobar or sub-lobar region will be expanded which may, in some cases, enhance delivery of a drug or permit more efficient lavage of the region. Alternatively, by elevating pressure within the "other"lung regions above that within the isolated region, the risk of migration of toxic therapeutic or other agents away from the isolated region can be greatly reduced.

According to the present invention, an isolation catheter comprises a catheter body having a proximal end, a distal end, and a main lumen therebetween. An expansible occlusion member is disposed at or near the distal end of the catheter body, and optical and illumination fibers are disposed in the catheter body to permit imaging of a region distal to the distal end of the catheter body when the catheter is in use. Usually, a hub will be attached to the proximal end of the catheter and include at least one connection port for the main lumen of the catheter. Optionally, the hub will contain a second connection pert for the optical and illumination fibers, and may contain further connection ports for other lumens and capabilities of the catheter, as described hereinafter.

The catheter body of the isolation catheter will be adapted and sized to allow advancement of the distal end of the catheter body to a target bronchial passage within the lung which is located distal to a first branching of the right or left main stem bronchus. Usually, at least a distal region of the catheter body will have an outer diameter which is sufficiently small and flexible to be advanced into bronchioles having a diameter below about 12 mm, preferably below about 10 mm, and often below about 8 mm. Exemplary catheter bodies will have a length in the range from 40 cm to 150 cm, preferably from 50 cm to 90 cm, an outer diameter in the range from 2 mm to 7 mm, preferably from 3 mm to 6 mm, and a main lumen diameter in the range from 1 mm to 6 mm, preferably from 2 mm to 4 mm. The expansible occlusion member will typically be an inflatable cuff or balloon having an expanded diameter in the range from 4 mm to 18 mm, preferably from 6 mm to 15 mm, and a length in the range from 5 mm to 30 mm, preferably from 10 mm to 15 mm. Usually, the catheter body will include at least one additional lumen for inflation of the inflatable cuff, and the additional lumen will be connected to an additional connector port on the catheter hub. Further optionally, the catheter body may include an additional lumen disposed to direct a washing fluid over a distal tip of the optical fiber which terminates at or near the distal end of the catheter body.

In a preferred aspect, systems according to the present invention comprises an isolation catheter as described above combined with an inner catheter to form a lung infusion/aspiration system. The inner catheter has a proximal end, a distal end, and a central lumen extending between the proximal end and distal end. The inner catheter is positionable within the main lumen of the isolation catheter so that the catheters may be used together in a co-axial fashion and further so that an annular lumen is formed within the main lumen of the isolation catheter, i.e., between an inner surface of the main lumen of the isolation catheter and an outer surface of the inner catheter. Optionally, the connector port on the isolation catheter has an additional connector port for the annular lumen. Alternatively, the system may comprise an adapter connectable to the hub on the isolation catheter, where the adapter has a connector port for the annular lumen. The dimensions and physical characteristics of the inner catheter will be chosen to permit introduction through the main lumen of the isolation catheter and farther to permit advancement of the inner catheter beyond the distal end of the isolation catheter into bronchial passages or bronchioles distal to the isolation catheter when in use.

An exemplary inner catheter has an outer diameter in the range from 0.5 mm to 4.5 mm, preferably from 1.5 mm to 3.5 mm, an inner lumen diameter in the range from 0.1 mm to 3.5 mm, preferably from 1 mm to 3 mm, and a length which is at least 10 cm longer than the isolation catheter in the system. Typically, the inner catheter will have a length in the range from 50 cm to 200 cm, preferably from 60 cm to 110 cm. Optionally, the inner catheter may have an expansible occlusion member disposed near its distal end to permit selective isolation of a lobar or sub-lobar region between proximal and distal points along the bronchial passages of the lung. Typically, the expansible occlusion member on the inner catheter is an inflatable cuff having an expanded diameter in the range from 4 mm to 18 mm, preferably from 6 mm to 15 mm, and a length in the range from 5 mm to 30 mm, preferably from 10 mm to 15 mm.

When including an inflatable cuff, the inner catheter will usually further comprise an inflation lumen disposed to deliver and remove an inflation medium to the inflatable cuff. Moreover, when provided with an inflatable cuff, the inner catheter will usually comprise an infusion/aspiration lumen having a distal port position proximally of the inflatable cuff so that substances, washing fluids, or the like, may be delivered or aspirated through the lumen between the inflatable cuff on the isolation catheter and the inflatable cuff on the inner catheter. Still further optionally, the inner catheter may comprise a vibratory element, such as an ultrasonic transducer, near its distal end to assist in dissolution of occlusive materials, enhance drug uptake, or the like. Still further optionally, the inner catheter may comprise two or more lumens, where at least two of the lumens are joined near a distal end to permit mixing of two or more gas or liquid streams which are being delivered through the catheter. The mixed streams are then released through a common outlet port on the inner catheter. Alternatively, the two streams may be delivered in parallel from the distal tip of the inner catheter for a variety of purposes.

The systems of the present invention may comprise further elements, such as guidewires, tracheal tubes with integral visualization (including both endotracheal and tracheostomy tubes), therapeutic or diagnostic reagents, and/or other system components intended to cooperate in performing the methods of the present invention as described in more detail below. Additionally, the systems of the present invention may be incorporated into kits where one or more system components are packaged together with instructions for use setting forth the methods described in more detail below. Such kits will usually further comprise packages for holding the system component(s) together with the instructions for use.

Methods according to the present invention comprise using an isolation catheter and an inner catheter (generally as described above) for isolating a lobar or sub-lobar region of the lung, and then performing a procedure within the isolated region. In a first instance, the methods are used for delivering a substance, typically a drug or other pharmaceutically active substance, to the isolated region. In a second instance, the methods are used for lavaging the isolated region, i.e., introducing and removing a washing liquid such as isotonic saline, alcohol, mucolytic agents, or the like, to the region. Optionally, the lavage and substance delivery methods can be combined where a drug or other active agent is included in the washing liquid which is being used for lavage. The methods of the present invention comprise positioning a distal end of the isolation catheter within a bronchial passage beyond a first branching within the right or left lung. The inner catheter is then positioned through the main lumen of the isolation catheter so that a distal end of the inner catheter lies in a bronchial passage distally beyond the distal end of the isolation catheter. At least one occlusion element near the distal end of the isolation catheter is expanded within the bronchial passage to isolate a target lobar or sub-lobar region. Thereafter, in the case of drug or other substance delivery, the substance may be delivered through the inner catheter to the isolated region of the lung. In the case of lavage, the washing liquid may be infused through either (or both) of the inner catheter or the isolation catheter and aspirated through the other (or both) of the two catheters. Infusion and aspiration may be performed sequentially or concurrently, or in combinations of both sequential and concurrent infusion and aspiration. Often, it will be preferred to infuse the washing liquid through the inner catheter so that it enters the isolated region generally in a distal portion thereof and diffuses or migrates back toward the isolation catheter where it is collected and removed. In some instances, the washing liquid drug, or other substance may be introduced as a bolus and held or retained within the isolated sub-lobar region for a pre-selected retention time prior to initiating aspiration. In other instances, it may be desirable to continuously both infuse and aspirate the washing liquid drug, or other substance to get a "circulation" of the substance through the isolated lobar or sub-lobar region. Optionally, the washing liquid may comprise a d-rug or other biologically active substance to perform a therapeutic action while the region is being lavaged.

In the case of substance delivery, the substance may comprise any one of a wide variety of pharmaceutical agents, including small molecule drugs, protein drugs, carbohydrate drugs, nucleic acid drugs (genes, optionally in combination with delivery vectors and/or expression control segments), and the like. The delivered substances may be in the form of an aerosol, optionally produced within the inner catheter or prior to introduction to the inner catheter. Still further optionally, the substance may comprise a liquid which is instilled through the inner catheter. For both substance delivery and lavage, it will frequently be preferred to position the isolation catheter and inner catheter through a visualizing endotracheal or tracheostomy tube which has been previously placed in the patient's trachea. Suitable visualizing endotracheal tubes are described, for example, in U.S. Pat. No. 5,285,778, the full disclosure of which is incorporated herein by reference. Usually, a visualizing endotracheal or tracheostomy tube will include an inflatable cuff or other occlusion element so that the whole lungs may be isolated from the upper regions of the trachea. In this way, the patient may be ventilated through the tracheal tube while other regions of the lung are isolated. Moreover, direct visualization at the bifurcation between the left and right lungs helps position in place the isolation catheter to the target region to be isolated. Additionally, the regions of the lung above or proximal to the occlusion element on the isolation catheter may be ventilated and maintained at a different pressure through the tracheal tube. Thus, by employing isolation cuffs on the tracheal tube, the isolation catheter, and the inner catheter, at least three isolated zones within the lung may be maintained with different pressures being simultaneously maintained. Moreover, different substances can be delivered to each of these regions through the lumens of the inner catheter, isolation catheter, and the tracheal tube, respectively. Often, pressure within the isolated region may be maintained higher than that within the proximal regions of the lung (where pressure is being controlled through the tracheal tube) resulting in expansion of the isolated region which may be beneficial for a variety of reasons. Alternatively, pressure within the isolated region may be maintained below that of the proximal portions of the lung, reducing the risk of release of materials from the isolated region into the proximal portions of the lung. Moreover, when the inner catheter has an isolation cuff, a third distal region of the lung may be pressurized separately from the intermediate and proximal regions.

Introduction of the isolation catheter and/or inner catheter will preferably be performed over a guidewire. The guidewire will first be introduced to a point beyond the location in a bronchial passage where it is desired to position a distal end of the isolation catheter and/or inner catheter. Preferably the isolation catheter will comprise optical and illumination fibers which permit direct visual observation of the guidewire as the guidewire and isolation catheter are advanced. In particular, the guidewire and isolation catheter can be advanced in tandem so that, as successive bifurcations are approached, the physician can steer a curved end of the guidewire into the desired branch bronchial passage. Aft(r positioning the isolation catheter at its desired final location, an occlusion cuff may be expanded and the inner catheter optionally introduced over the guidewire or introduced directly through the main lumen of the isolation catheter without a guidewire. While the inner catheter may in some instances incorporate optical and illumination fibers, it will usually not have such imaging capabilities. Thus, positioning of the inner catheter will frequently be done solely by observation from the isolation catheter and/or under fluoroscopic or other external imaging. Of course, positioning of an isolation catheter can also be performed solely under fluoroscopic imaging (or in combination with both direct visual and fluoroscopic imaging), particularly when the isolation catheter does not include imaging capability.

In a further specific aspect of the methods of the present invention, the inner catheter may be moved and repositioned within the bronchial passages of the isolated region to deliver a substance or release a washing fluid for lavage at different points within the region. Optionally, the inner catheter can be moved (i.e., advanced distally or drawn proximally) while the substance or washing liquid is being released in order to better distribute the material within the isolated region. Further optionally, the inner catheter could also be moved through the isolated region in order to aspirate materials which have been introduced, either alone or in combination with aspiration through the main lumen of the isolation catheter.

Kits according to the present invention include at least an isolation catheter, and optionally include an inner catheter, a tracheal tube, and/or a guidewire. Other components including medical and bioactive reagents, e.g., drugs, washing liquids, or the like, may also be provided within the kits. In addition to the isolation catheter and optional other system components, the kits will comprise instructions for use setting forth a method of the present invention as generally set forth above. The kits will usually be packaged together in conventional medical packaging, such as a pouch, tray, tube, box, bag, or the like. Instructions for use may be provided on a separate printed sheet, or may printed in whole or in part on the packaging materials. When printed separately, the instructions are commonly referred to as a package insert. Usually, at least the isolation catheter and other components of the kit which would be used in the procedure will be packaged in a sterile manner within the kit.

BRIEF DESCRIPTION OF THE DRAWINGS

FIG. 1 is a side view of a sub-lobar isolation catheter constructed in accordance with the principles of the present invention.

FIG. 1A is a cross-sectional view taken along line 1A—1A in FIG. 1.

FIG. 1B is an alternative cross-sectional view similar to that shown in FIG. 1A.

FIG. 2 is a side view of a first alternative construction of a sub-lobar catheter constructed in accordance with the principles of the present invention.

FIG. 2A is a cross-sectional view taken along line 2A—2A of FIG. 2.

FIG. 3 is a side view of a second alternative construction of a sub-lobar catheter constructed in accordance with the principles of the present invention.

FIG. 3A is a cross-sectional view taken along line 3A—3A of FIG. 3.

FIG. 6 illustrates a first alternative construction of the inner catheter of the resent invention.

FIG. 6A is a cross-sectional view taken along line 6A—6A of FIG. 6.

FIG. 7 is a second alternative construction of the inner catheter of the resent invention.

FIG. 7A is a cross-sectional view taken along line 7A—7A of FIG. 7.

DESCRIPTION OF THE SPECIFIC EMBODIMENTS

Figure 4:
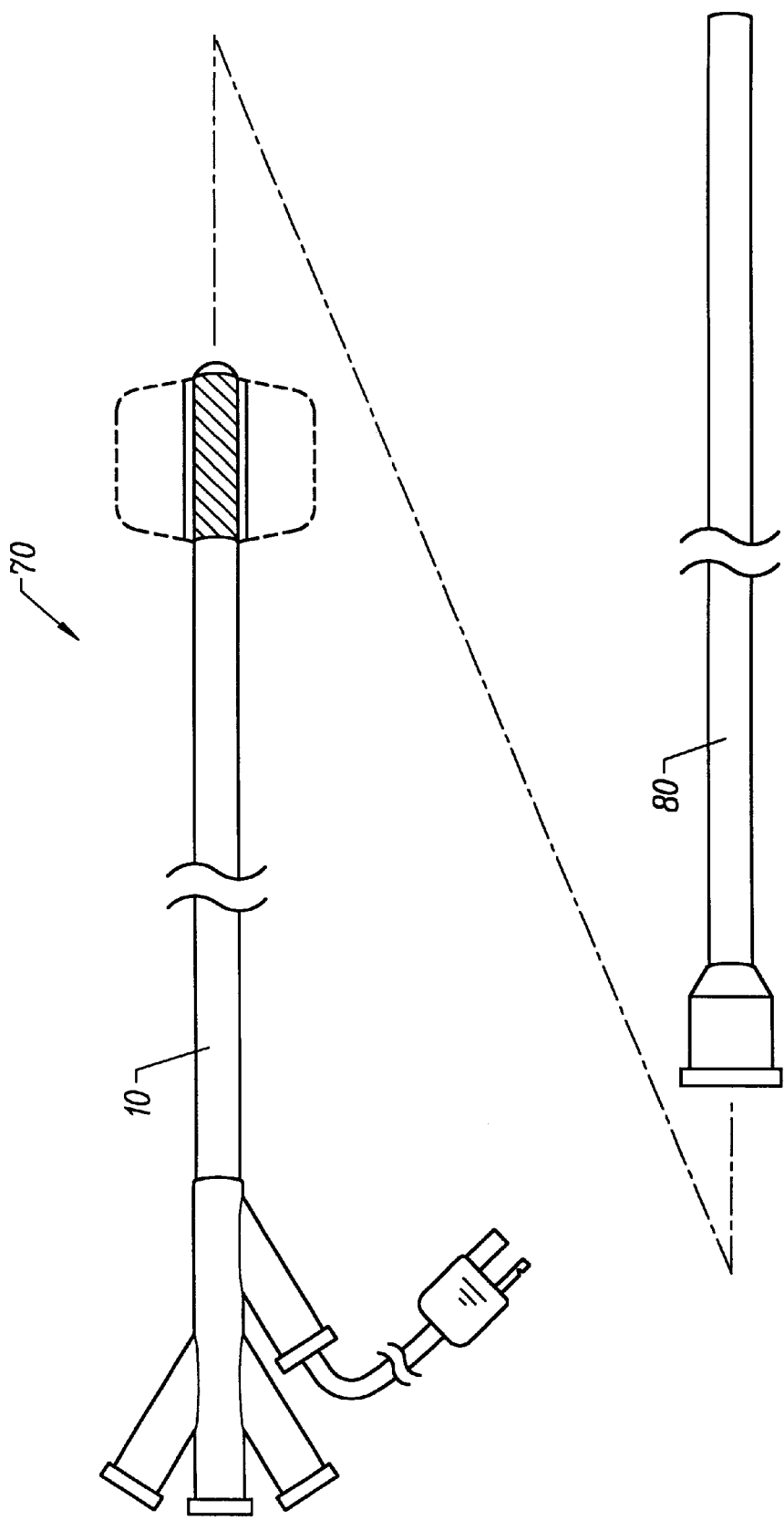
FIG. 4 illustrates a system comprising a sub-lobar isolation catheter and an inner catheter constructed in accordance with the principles of the present invention.

Isolation of a lobar or sub-lobar region of the lung is accomplished by occluding a lumen of a bronchial passage (bronchiole) at a location distal to a first branch in the network of bronchial passages within the right or left lung. Substances may be delivered to and/or a washing fluid may be used to lavage the isolated lobar or sub-lobar region of the lung by introducing or exchanging materials through a lumen of an isolation catheter, usually in combination with delivery or exchange through a lumen of an associated inner catheter. An inflatable cuff or other expansible isolation element on the isolation catheter is positioned at an isolation location within the bronchial passage, and the cuff inflated. The inner catheter is then positioned at a desired location distal to the end of the isolation catheter, and the isolated region is thus accessible through at least two access lumens, i.e., one lumen through the inner catheter and a second annular lumen between the exterior of the inner catheter and the interior luminal wall of the isolation catheter. These access lumens may be used separately or in combination in a variety of ways to perform the methods of the present invention. The apparatus and methods of the present invention will now be described in greater detail.

Referring to FIGS. 1 and 1A, an isolation catheter 10 comprises a catheter body 12 having a proximal end 16 and a distal end 14. An inflatable isolation cuff 18 is disposed near the distal end 14 of the catheter body 12, and an inflation lumen 20 extends through the catheter body from a proximal port 22 on proximal hub 24 to the balloon 18. The catheter 10 further comprises an optical fiber or bundle 24 and an illumination fiber or bundle 26, both of which are brought out to a suitable connector 28 through a connecting cable 30. The optical fiber 24 and illuminating fiber 26 may be plugged into a variety of conventional imaging consoles which can provide a real time, visual image looking forwardly from the distal end 14 of the catheter body 12. Suitable commercial imaging consoles are available from suppliers, such as Pulmonx, Palo Alto, Calif., assignee of the present application as well as Olympus, Pentax and Stryker. The catheter body 12 further includes a main lumen 32 which extends the entire length of the catheter body and passes through connector hub 36 to proximal connector 34. As will be discussed in more detail below, the main lumen 32 can be used for introducing and/or aspirating materials which are introduced to or withdrawn from an isolated lobar or sub-lobar region of the lung. Most usually, the main lumen 32 will receive an inner catheter (FIGS. 4 and 5 below), and the isolation catheter and inner catheter will be utilized together for delivering, collecting, and removing materials from an isolated sub-lobar region of the lung.

As shown in FIGS. 1 and 1A, the catheter body 12 of the isolation catheter 10 is a single extrusion having four lumens or passages formed therein. Two of the lumens form the inflation lumen 20 and the main lumen 32, while the other two lumens house the optical fiber bundle 24 and the illumination fiber bundle 26. The catheter body 12 could also be formed from a plurality of separate tubular members which are held together by an outer cover, as illustrated in FIG. 1B. For example, an inner tube 40 can be disposed in parallel with the optical fiber bundle 24 and the illuminating fiber bundle 26. A separate tubular member 42 can also be placed co-axially on the exterior of tube 40, and all of the components held together by a cover 44 which may, for example, be shrink-wrapped over the assembly. An inflation lumen 46 is then provided in the space under the cover 44 which is unoccupied by the optical and tubular components. A variety of other specific construction designs may also be provided.

The catheter body 12 may be formed from conventional materials, such as polyamides (nylons), polyethylenes, polyurethanes, polytetrafluoroethylenes (PTFEs), polyimides, and the like. The inflatable cuff can be formed from other conventional materials, such as polyvinylchloride, polyurethanes, high density polyethylenes, low density polyethylenes, nylons, PTFEs, and the like. Exemplary and preferred dimensions for the catheter body 12 of the isolation catheter 10 have been set forth above.

A second exemplary isolation catheter 50 constructed in accordance with the principles of the present invention is illustrated in FIGS. 2 and 2A. The construction of isolation catheter 50 is generally the same as that for isolation catheter 10, and like components will be given like numbers. The principal difference between the catheters 50 and 10 is that catheter 50 includes a lens washing lumen 52 which extends from lens washing port 54 in the hub 56 to a position at the distal tip of the catheter body which lies immediately over a lens (not shown) formed at the distal end of the optical fiber or bundle 26. Because of the humid and contaminating nature of the lungs, it will be a significant benefit to be able to wash the optical viewing lens whenever the lens becomes obscured due to condensation or fouling.

A third exemplary construction of the isolation catheter of the present invention is illustrated in FIGS. 3 and 3A. There, an isolation catheter 60 comprises generally the same components as catheters 10 and 50, except that catheter body 12 further includes a lumen 62 which receives a guidewire (or alternatively an articulating steering mechanism) and which extends from port 64 on hub 66 to the distal end 14 of the catheter body 12. Thus, isolation catheter 60 is specially adapted for introduction over a guidewire (or other steering mechanism) according to the methods of the present invention and as described in more detail below. It will be appreciated, of course, that the earlier embodiments could also be introduced over a guidewire where the guidewire is passed through the main lumen 32, but in such cases the main lumen would have to be emptied i.e., the inner catheter (if used) would have to be removed from the isolation catheter. Optionally, the isolation catheter 60 can also include a vibratory element 66 near its distal end. The vibratory element could be a mechanically driven surface, but will usually comprise an ultrasonic transducer intended to deliver vibratory energy to disrupt blockages in the bronchus, enhance drug delivery, or the like.

Figure 5:
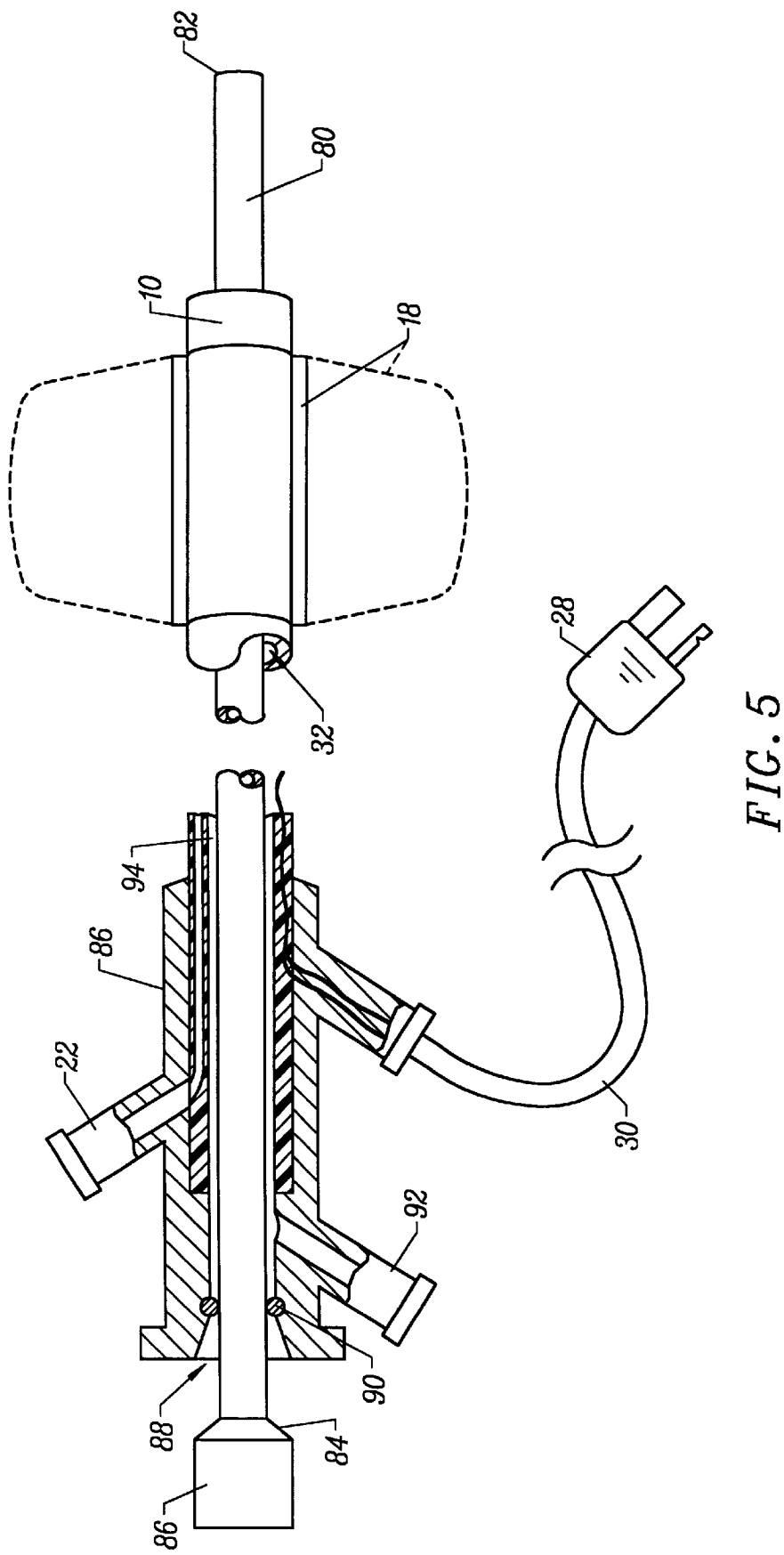
FIG. 5 is a side view of the inner catheter of FIG. 4 mounted within the sub-lobar isolation catheter, with portions broken away.

Systems 70 according to the present invention comprise an isolation catheter 10 (or any of the other isolation catheters described above or which would come within the principles of the present invention) and an inner catheter 80. As illustrated in FIGS. 4 and 5, the inner catheter 80 is sized and adapted to fit within the main lumen 32 of the isolation catheter 10. The inner catheter 80 has a distal end 82 and a proximal end 84 which terminates in a connecting hub 86. The isolation catheter 10 includes a hub 96 which is similar to the previously described hubs, except that a proximal end has been modified to slidably receive the inner catheter 80. As shown, an O-ring 90 is provided to provide a sliding pneumatic or hydraulic seal about the inner catheter. Additionally, an access port 92 is provided in the hub 96 to permit communication with the annular lumen 94 disposed between the exterior of inner catheter 80 and the interior of the main lumen 32 of the isolation catheter 10. In this way, materials can be withdrawn or introduced through the isolation catheter 10 as well as through the lumen of the inner catheter 80. More particularly, it permits two spaced-apart access points, i.e., at the distal ends of the isolation catheter 10 and inner catheter 80, respectively, to be established within an isolated lobar or sub-lobar region of the lungs. Using two access points, a variety of substance delivery and lavage protocols can be run, as described in more detail below.

A first alternative embodiment of an inner catheter 100 is illustrated in FIGS. 6 and 6A. Inner catheter 100 includes catheter body 102 having an inflatable isolation cuff 104 near its distal end. A plurality of infusion/aspiration ports 106 are also formed near the distal end 103 of the catheter body 102 and are connected by a lumen 108 to an aspiration/infusion port 110 in proximal hub 112. The inflatable cuff 104 may be inflated by connecting a suitable inflation source to connector 114 which delivers the inflation medium through lumen 116 to the cuff 104. A central lumen 120 extends the length of the catheter body from its distal end 103 to a connection port 122 in the hub 112. By providing the infusion/aspiration ports 106 proximal to the inflatable cuff 104, it will be appreciated that substances may be delivered or removed from a region which is proximal to the cuff 104 but distal to the isolation cuff on the isolation catheter with which the inner catheter 100 is used.

Yet a further alternative embodiment of an inner catheter 130 is illustrated in FIGS. 7 and 7A. The inner catheter 130 includes an ultrasonic or other vibratory element 132 (shown in broken line) at or near its distal end 134. The ultrasonic element 132 may be positioned at the distal end of a lumen 136 which extends through the length of the catheter 130. The lumen 136 may thus hold wires necessary to power the ultrasonic transducer, where the wires are brought out through a connecting cable 140 and terminate in a plug 142. An aspiration/infusion lumen 150 also extends the length of the catheter 130 and terminates in a luer or other connector 152 at the proximal end of the catheter. Optionally, a similar ultrasonic or other vibratory element may be disposed on the isolation catheter, either in addition to or in place of the vibration element 132 on the inner catheter. Although shown proximal to cuff 18, the vibratory element 66 may also be placed distal to the cuff to deliver energy into an isolated region.

Figure 8:
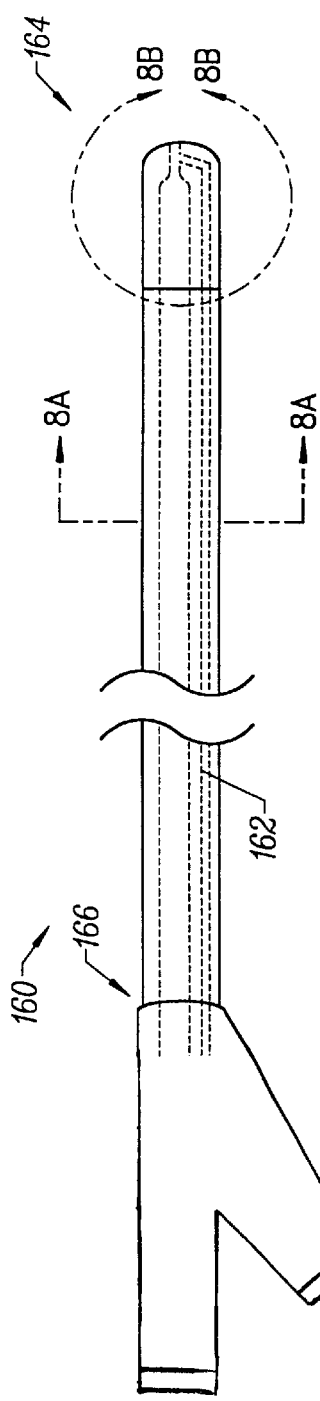
FIG. 8 is a third alternative construction of the inner catheter of the present invention.
Figure 8B:
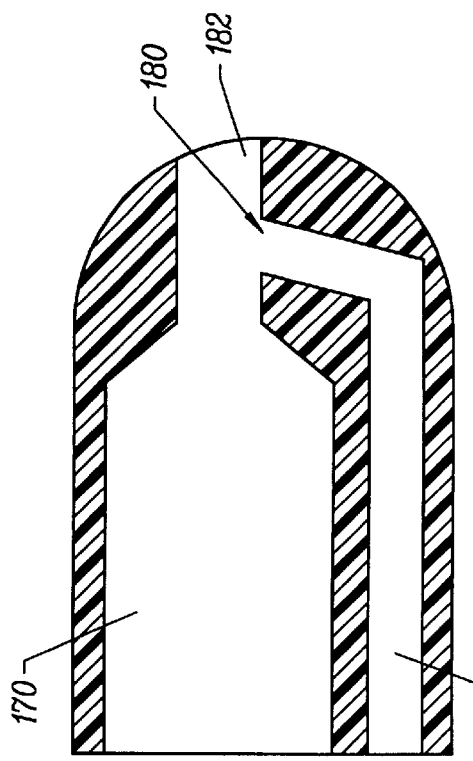
FIG. 8B is a detailed view of the distal end of the catheter of FIG. 8 taken along line 8B—8B of FIG. 8.
Figure 8A:
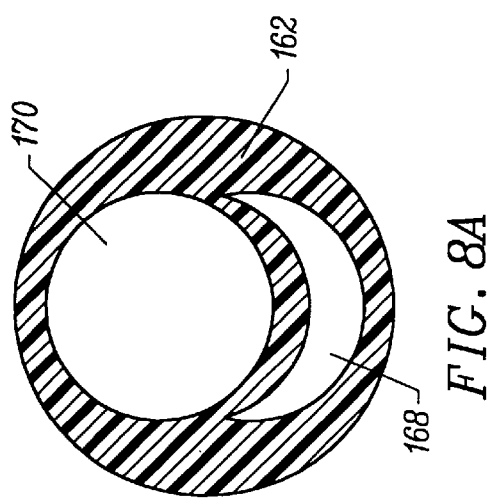
FIG. 8A is a cross-sectional view taken along line 8A—8A of FIG. 8.

Referring now to FIGS. 8, 8A, and 8B, still a further embodiment of an inner catheter 160 will be described. The catheter 160 comprises a catheter body 162 having a distal end 164 and a proximal end 166. A pair of lumens 168 and 170 extend the length of the catheter body 162 from ports 172 and 174, respectively, and proximal hub of 176 to each of the lumens 168 and 170 is suitable for delivering a material, either liquid, aerosol, or solid (in some flowable form), from the ports 172 and 174 to a mixing region 180 near a distal instillation port 182 at a distal tip of the catheter. For example, air or other gas may be delivered through the larger lumen 170 so that it flows the mixing area 180. By delivering a liquid or powder through the smaller lumen 168, the airflow can act as a Venturi in suspending an aerosolizing material which is delivered to the mixing area. In this way, droplets or particulates can be delivered or instilled directly within an isolated lobar or sub-lobar region of the lung. By properly controlling the particulate or droplet size, i.e., to arrange generally between 0.1 µm to 5 µm, absorption of these materials into the alveolar regions of the lungs can be enhanced. By controlling the particulate or droplet size outside this range, usually above 5 µm, preferably above 10 µm, local delivery (i.e., not systemically absorbed) of a drag or other substance can be achieved.

Figure 9:
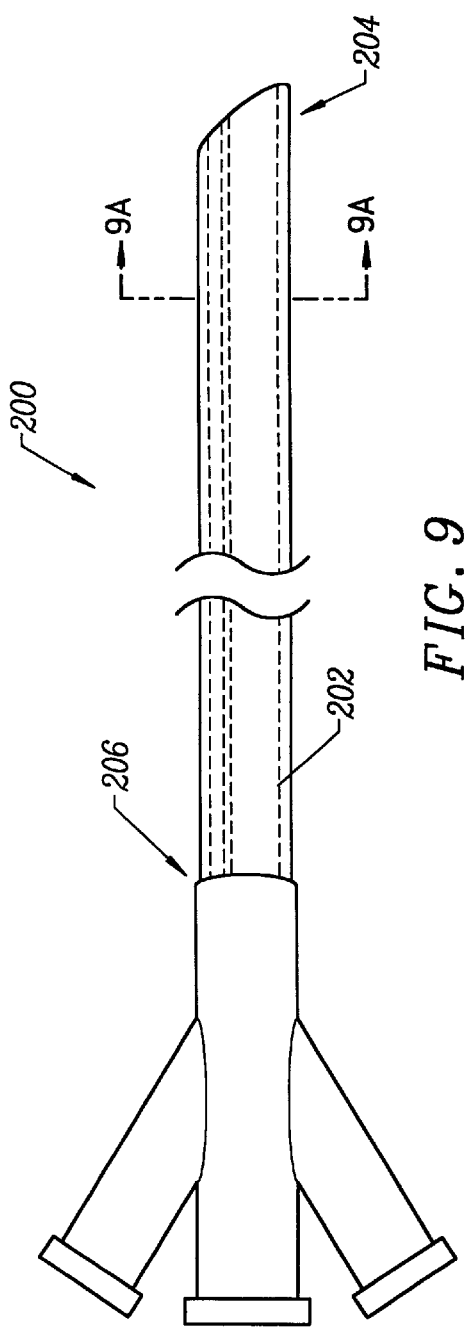
FIG. 9 is a fourth alternative construction of the inner catheter of the present invention.
Figure 9A:
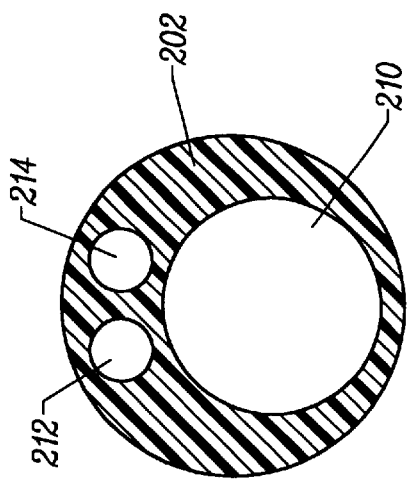
FIG. 9A is a cross-sectional view taken along line 9A—9A of FIG. 9.
Figure 10:
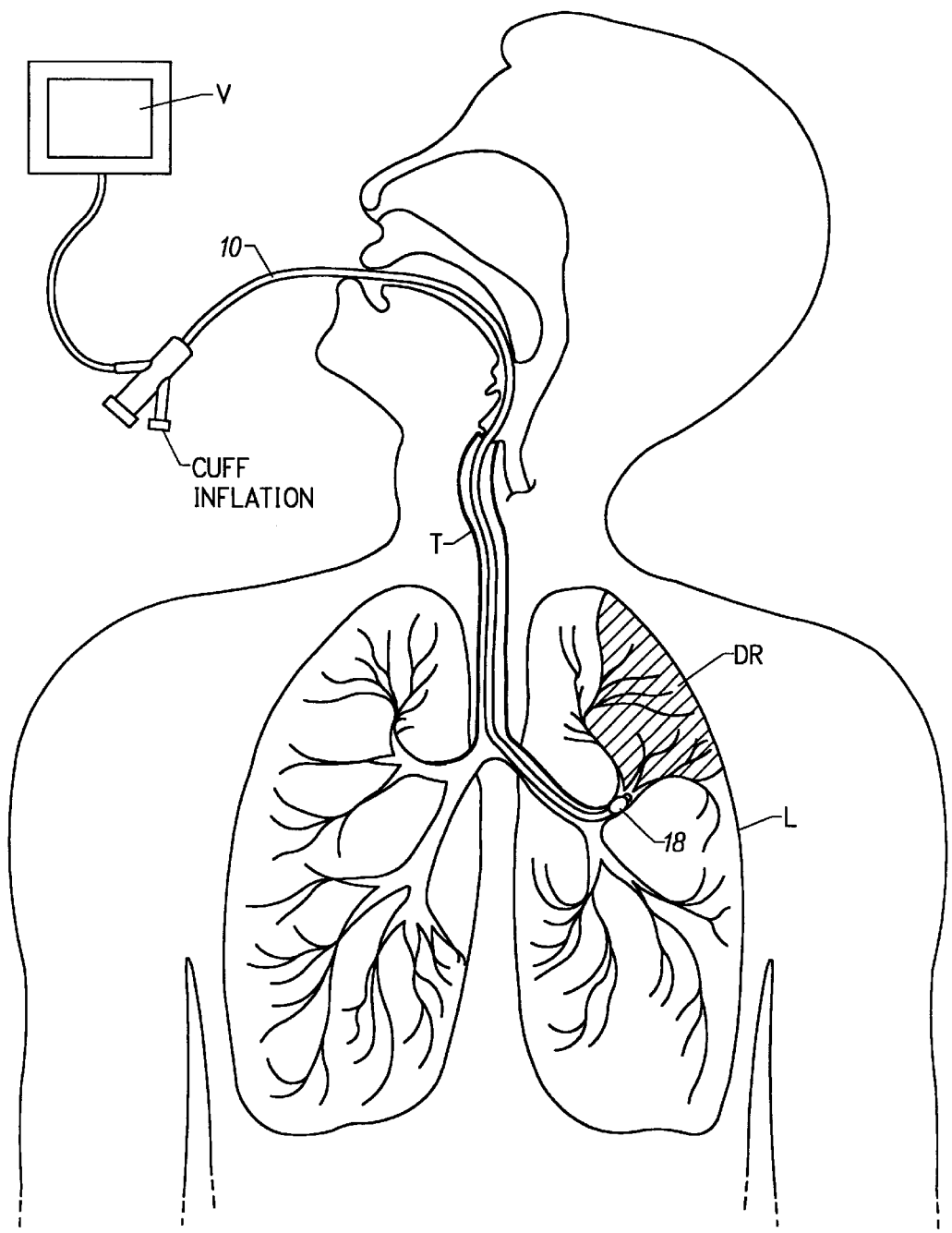
FIG. 10 illustrates introduction of a sub-lobar isolation catheter to a diseased region within a lung according to the method of the present invention.
Figure 11:
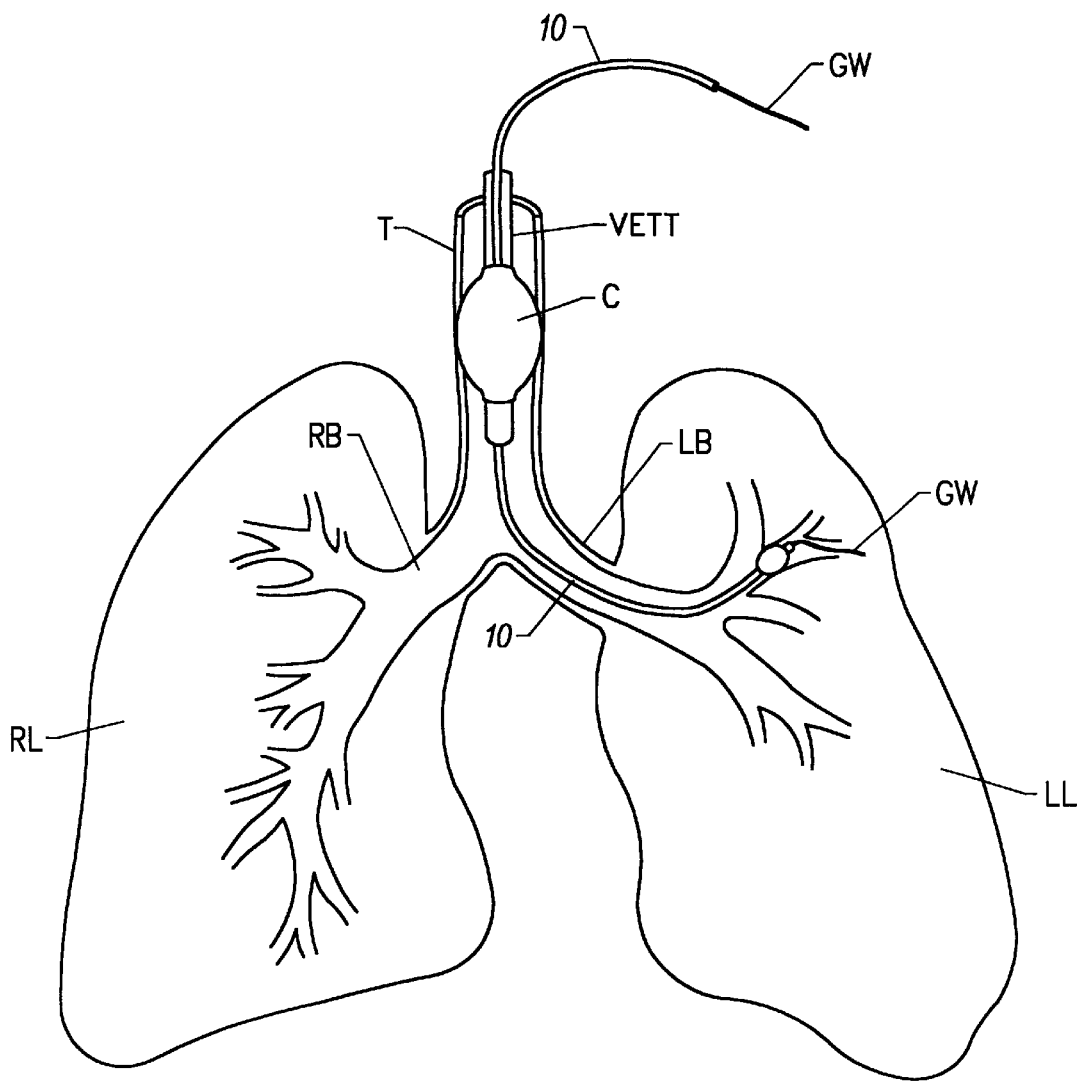
FIG. 11 is a detailed view of the introduction of FIG. 10 shown with the isolation catheter being passed through a visualizing endotracheal tube.
Figure 12A:
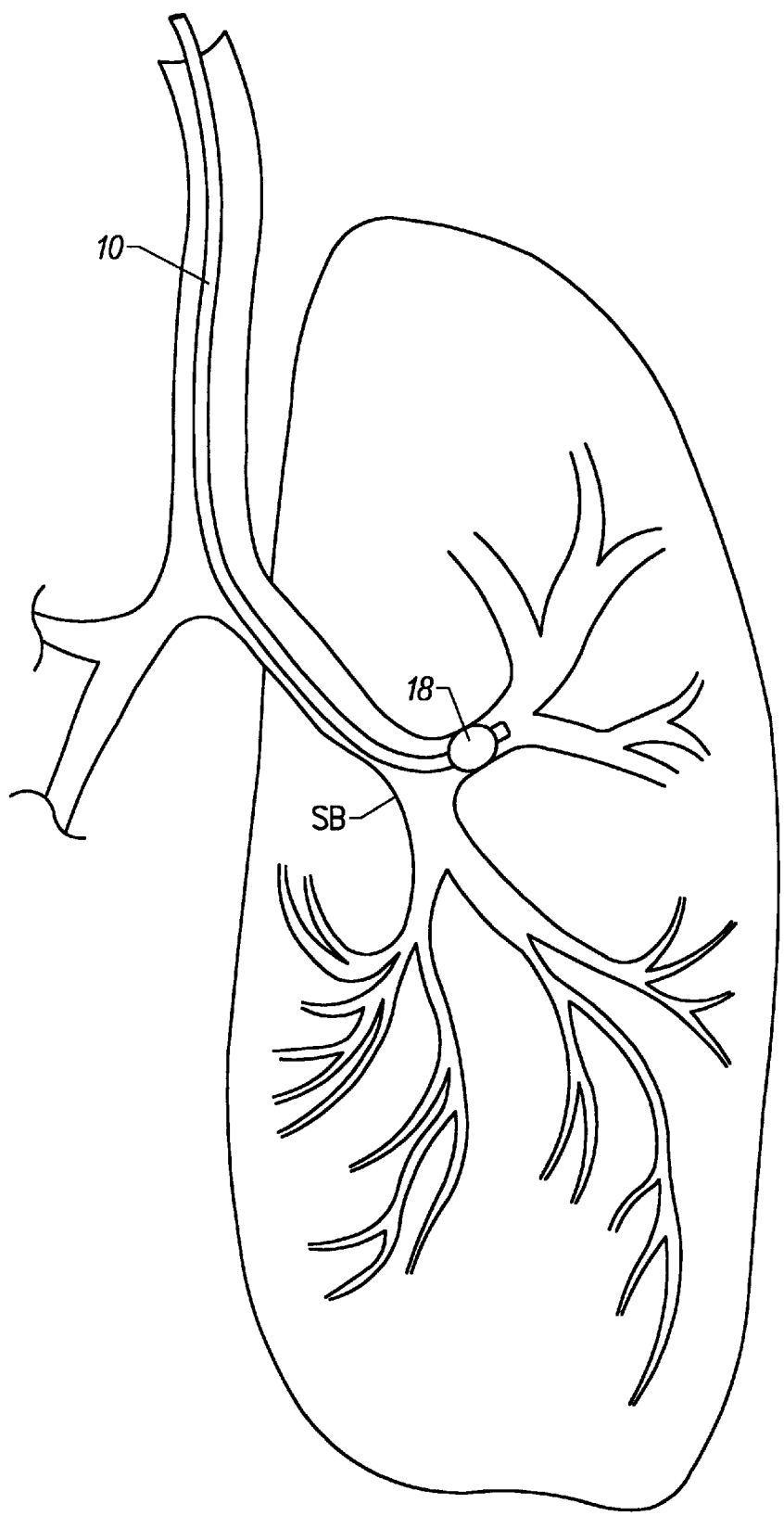
FIGS. 12A–12C illustrate use of the various inner catheters for performing particular procedures in accordance with the principles of the present invention.
Figure 12B:
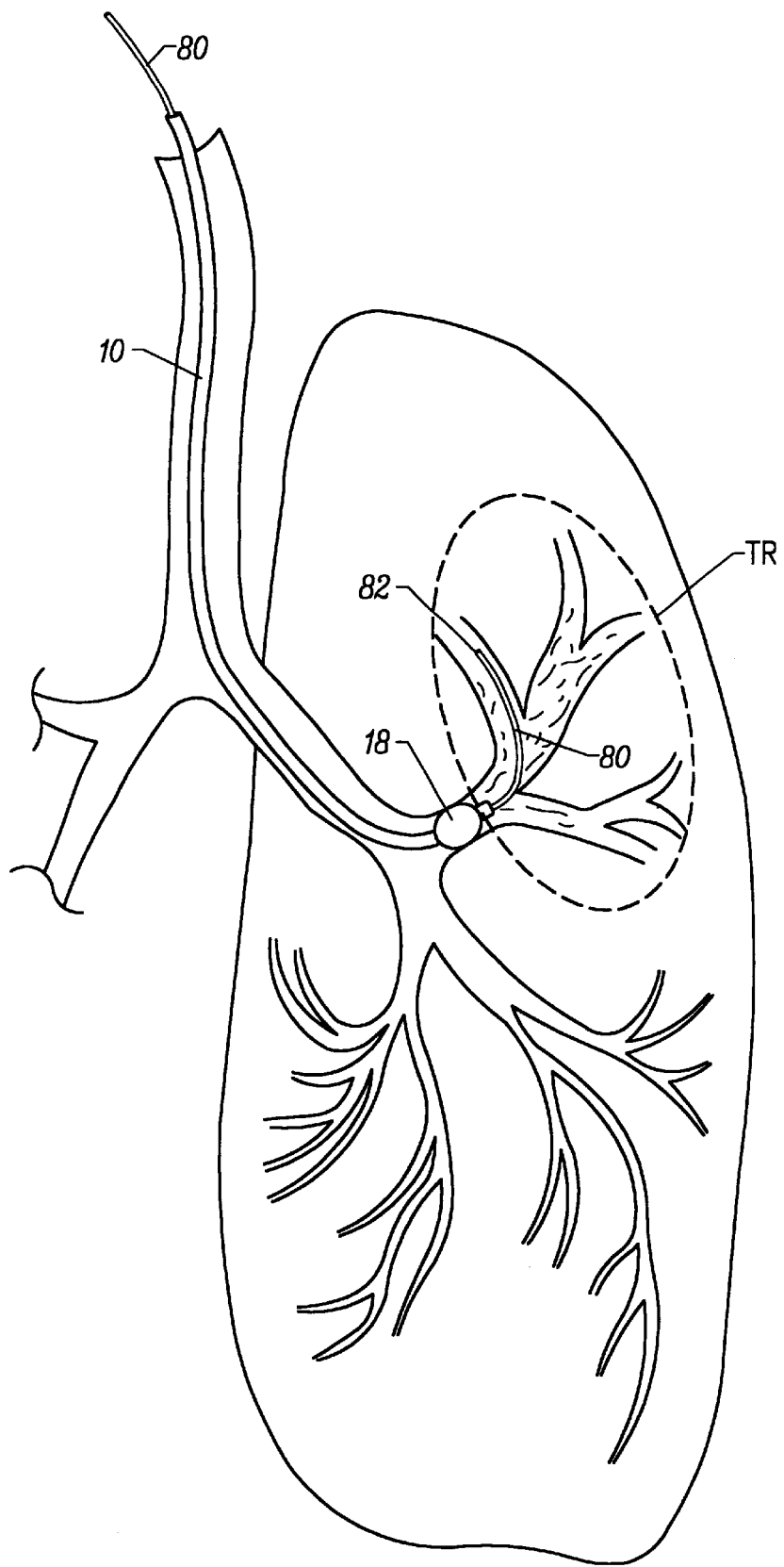
Figure 12C:
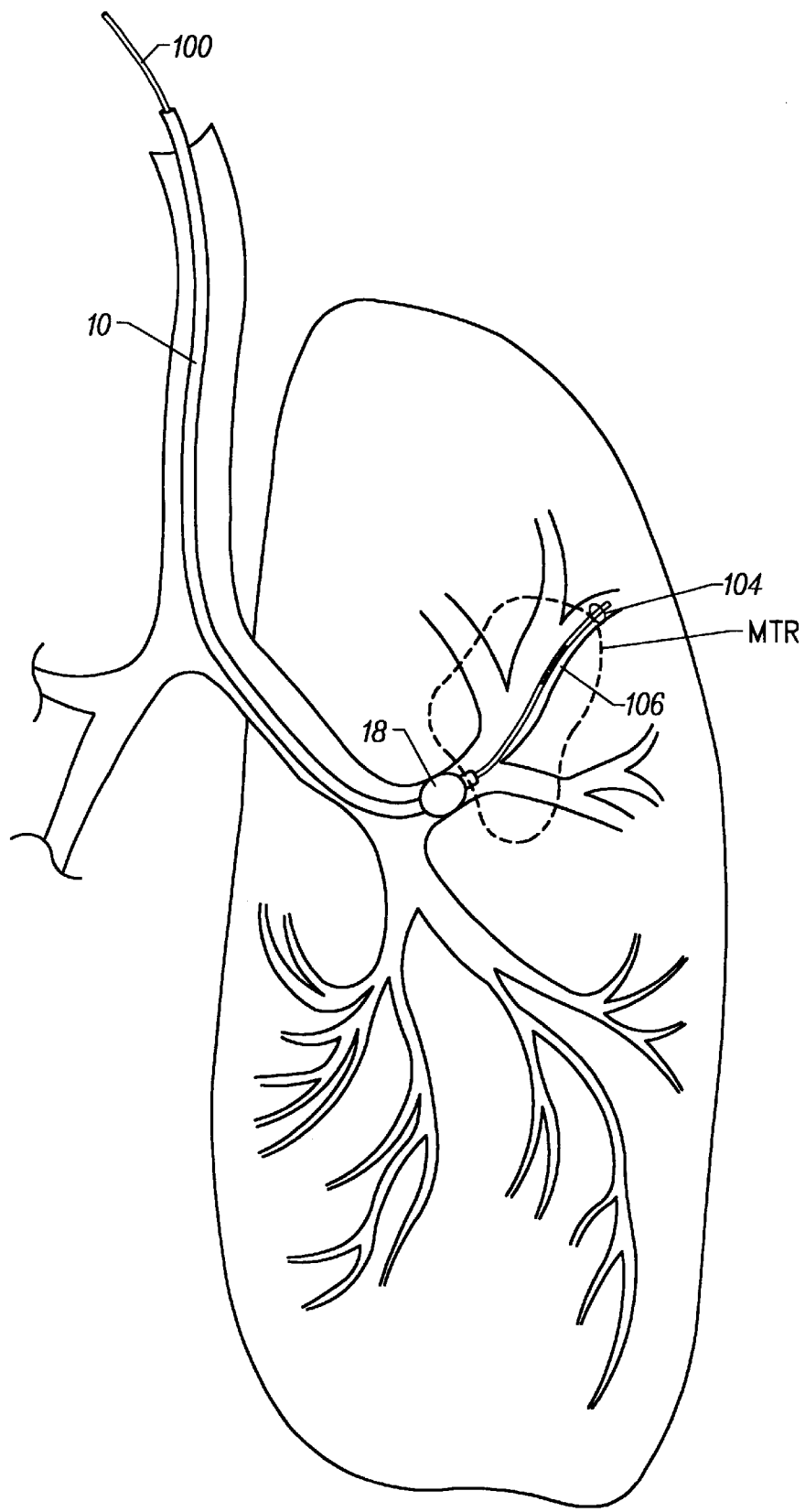
Figure 13:
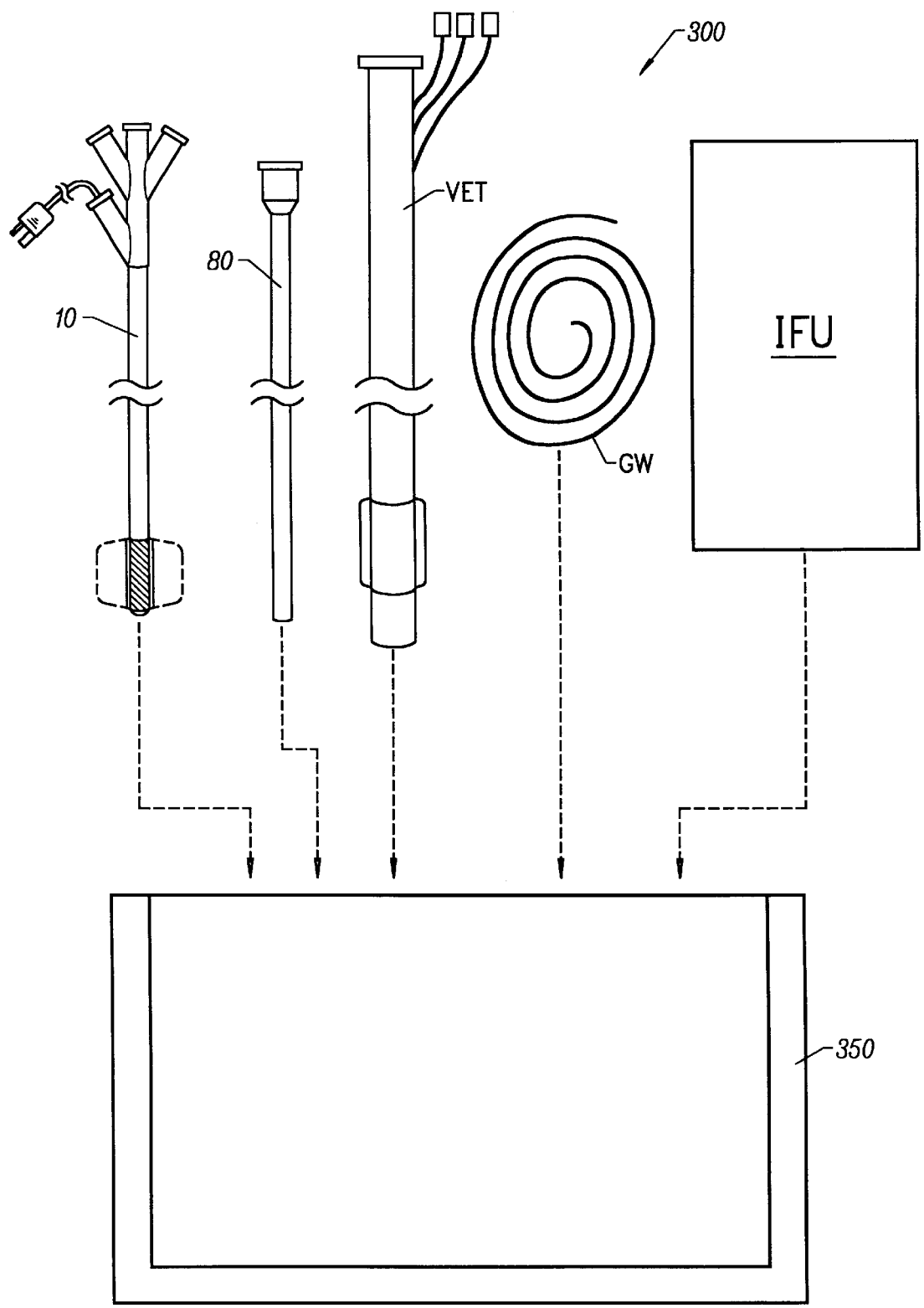
FIG. 13 illustrates a kit constructed in accordance with the principles of the present invention.

Referring now to FIGS. 9 and 9A, still yet a further embodiment of an inner catheter 200 constructed in accordance with the principles of the present invention will be described. The inner catheter 200 comprises a catheter body 202 having a distal end 204 and a proximal end 206. The catheter body includes a central lumen 210 and a pair of instillation lumens 212 and 214. The catheter would be suitable for aerosolization of substances, particularly by delivering a liquid or solid powder substance through one of the lumens 212 and air or other aerosolization gas through the other lumen 214. The central lumen 210 could be used for aspiration, delivery of other drug materials, or the like.

Referring now to FIGS. 10, 11, and 12A–12C, methods according to the present invention will be described. Most generally, an isolation catheter 10 may be introduced through the mouth, the trachea T and into a lobe L of the lung until it reaches a diseased region DR. Alternatively, the isolation catheter 10 could be introduced through an incision in the neck, usually through a tracheostomy tube. At that point, cuff 18 may be inflated to isolate regions of the lung distal to the inflated cuff in the bronchial passage. As illustrated in. FIG. 11, catheter 10 may optionally be delivered through a visualizing endotracheal tube VETT (or visualizing tracheostomy tube), where a cuff C on the tube is inflated within the trachea T at a region just above the main lung bifurcation into the right and left lungs RL and LL. Further optionally, the isolation catheter 10 may be advanced over a guidewire GW, where visualization of the guidewire immediately ahead of the catheter may be observed on the video screen V attached to the optical and illumination fibers within the catheter 10. In particular, the guidewire may be advanced just ahead of the distal end of the catheter 10 in tandem so that the guidewire can be observed as it is rotated and introduced selectively into the bronchial passages at bifurcations. Alternatively, or additionally, advancement of the catheter 10 may be observed fluoroscopically or using any other available external imaging systems.

Once the catheter 10 is in place beyond a second bifurcation SB in the bronchial passages, as illustrated in FIG. 12A, the inflatable cuff 18 may be inflated to both anchor the distal end of the catheter and isolate regions of the lung distal thereto. After the cuff 18 is inflated, the inner catheter 80 may be advanced through the main lumen 34 so that the distal end 82 of the inner catheter progresses distally into a desired bronchial passage. Advancement of the distal end 82 may optionally be over a guidewire and will usually be performed under visual imaging using the optical illuminating fibers in the isolation catheter 10. Once the inner catheter has been properly positioned, as shown in FIG. 12B, a desired procedure can be performed. For example, a drug can be delivered through the distal end 82 of the inner catheter to treat a target region TR, shown in broken line in FIG. 12B, additionally or alternatively, the target region TR can be lavaged by introducing a washing fluid through either catheter 10 or 80 and/or collecting the fluid through either of catheter 10 or 80.

Alternatively, as shown in FIG. 12C, inner catheter 100 having inflatable cuff 104 at its distal end may be introduced through the isolation catheter 10. By then inflating cuff 104 distally relative to cuff 18 on isolation catheter 10, a modified target region MTR can be defined. In particular, the target region MTR in FIG. 12C will be more limited in volume than that formed in FIG. 12B where there is no distal isolation. Use of the second isolation cuff 104 on the inner catheter 100 permits much more specifically focused treatment protocols, both drug delivery and lavage, to be performed. By delivering or aspirating the materials through the ports 106, it will be appreciated that the treatment is substantially limited to between the two cuffs 18 and 104.

Referring now to FIG. 13, a kit 300 according to the present invention will comprise at least a lobar or sub-lobar isolation catheter 10 and an inner catheter 80 together with instructions for use IFU. Optionally, the kits may further include other system components as described above, such as a visualizing endotracheal tube VET, a guidewire GW, and/or various reagents (not shown). The instructions for use IFU will set forth any of the methods as described above, and all kit components will usually be packaged together in a suitable package 350, such as a pouch, tray, tube, box, bag, or the like. Usually, those kits components, such as the isolation catheter 10 and inner catheter 80, which will be used in performing the procedure on the patient, will be sterilized and maintained sterilely within the kit. Optionally, separate pouches, bags, trays, or other packaging materials may be provided within a larger package, where the smaller packs may be separately opened and will separately maintain the components in a sterile fashion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a substance to an isolated region of the lung, said method comprising:

positioning a visualizing tracheal tube in a trachea;

positioning a distal end of an isolation catheter through a lumen of the visualizing tracheal tube within a bronchial passage beyond a first branching within a right or left lung;

positioning an inner catheter through a main lumen of the isolation catheter so that a distal end of the inner catheter lies in a bronchiole distally beyond the distal end of the isolation catheter;

expanding an occlusion element near the distal end of the isolation catheter within the bronchial passage to isolate a target region;

providing a substance; and delivering the substance through the inner catheter to the isolated region of the lung.

2. A method as in claim 1, wherein the substance comprises pharmaceutical.

3. A method as in claim 1 or 2, wherein the substance comprises an aerosol or gas.

4. A method as in claim 1 or 2, wherein the substance comprises a liquid.

5. A method as in claim 1, further comprising aspirating the substance through the isolation catheter.

6. A method as in claim 1, further comprising expanding an occlusion cuff on the visualizing tracheal tube and controlling ventilation of the patient's lungs through the visualizing tracheal tube.

7. A method as in claim 6, wherein the isolated region and the remainder of the lung are maintained at different pressures.

8. A method as in claim 7, wherein the pressure within the isolated region is maintained at a higher pressure than the remainder of the lung.

9. A method as in claim 7, wherein the pressure within the isolated region is maintained at a lower pressure than the remainder of the lung.

10. A method as in claim 1, further comprising positioning a guidewire to a point beyond the location in the bronchial passage where the occlusion element is to be expanded, wherein positioning the isolation catheter comprises introducing the isolation catheter over the guidewire.

11. A method as in claim 10, further comprising viewing the guidewire using optical and illumination fibers carried by the isolation catheter as the guidewire is steered through bifurcations in the lungs.

12. A method as in claim 10, further comprising viewing the guidewire fluoroscopically as the guidewire is steered through bifurcations in the lung.

13. A method as in claim 1, further comprising drawing or advancing the inner catheter through the bronchiole while delivering the substance.

14. A method as in claim 1, further comprising repositioning the inner catheter within the isolated region and delivering the substance to two or more locations.

15. A method as in claim 1, further comprising expanding an occlusion element near the distal end of the inner catheter to isolate a distal portion of the bronchial passage so that an isolated region is disposed between the occlusion element on the isolation catheter and the occlusion element on the inner catheter.

16. A method as in claim 15, wherein the substance is delivered through one or more delivering ports on the inner catheter proximal to the occlusion element.

17. A method for lavaging an isolated region of a lung, said method comprising:

positioning a visualizing endotracheal tube in a trachea;

positioning a distal end of an isolation catheter through a lumen of the visualizing tracheal tube within a bronchial passage beyond a first branching within a right or left lung;

positioning an inner catheter through a main lumen of the isolation catheter so that a distal end of the inner catheter lies in a bronchiole distally beyond the distal end of the isolation catheter;

expanding an occlusion element near the distal end of the isolation catheter within the bronchial passage to isolate a target region of the lung;

infusing a washing liquid through one of the inner catheter or the isolation catheter to the isolated region of the lung; and aspirating the washing liquid from the isolated region through the other of the inner catheter or the isolation catheter.

18. A method as in claim 17, wherein the washing liquid is infused through the inner catheter and aspirated through the isolation catheter.

19. A method as in claim 17, wherein the washing liquid is infused through the isolation catheter and aspirated through the inner catheter.

20. A method as in claim 17, wherein the washing liquid is alternately infused through the inner catheter and the isolation catheter and aspirated through the isolation catheter and the inner catheter.

21. A method as in claim 17, wherein a bolus of the washing liquid is introduced and held within the isolated region for a retention time period prior to initiating aspiration.

22. A method as in claim 17, wherein the infusing and the aspirating of the washing liquid are performed simultaneously.

23. A method as in claim 17, wherein the washing liquid comprises a pharmaceutical substance.

24. A method as in claim 17, further comprising expanding an occlusion cuff on the visualizing tracheal tube and ventilating the patient's lungs through the visualizing tracheal tube at a controlled pressure.

25. A method as in claim 24, further comprising controlling pressure of the target isolated region, wherein the isolated region and the remainder of the lung may be controlled at different pressures.

26. A method as in claim 25, wherein the pressure within the isolated region is maintained at a higher pressure than the remainder of the lung.

27. A method as in claim 25, wherein the pressure within the isolated region is maintained at a lower pressure than the remainder of the lung.

28. A method as in claim 17, further comprising positioning a guidewire to a point beyond the location in the bronchial passage where the occlusion element is to be expanded, wherein positioning the isolation catheter comprises introducing the catheter over the guidewire.

29. A method as in claim 28, further comprising viewing the guidewire using optical and illumination fibers carried by the isolation catheter as the guidewire is steered through bifurcations in the lungs.

30. A method as in claim 28 further comprising viewing the guidewire fluoroscopically as the guidewire is steered through bifurcations in the lung.

31. A method as in claim 17, further comprising drawing or advancing the inner catheter through the bronchiole while delivering the washing liquid.

32. A method as in claim 17, further comprising repositioning the inner catheter within the isolated region and delivering the washing liquid to two or more locations.

33. A method as in claim 17, further comprising expanding an occlusion element near the distal end of the inner catheter to isolate a distal portion of the bronchial passage so that the isolated region is disposed between the occlusion element on the isolation catheter and the occlusion element on the inner catheter.

34. A method as in claim 33, wherein the washing liquid is delivered through one or more delivering ports on the inner catheter proximal to the occlusion element.

* * * * *